US006059716A

United States Patent [19]

Lee et al.

[11] Patent Number: 6,059,716

[45] Date of Patent: May 9, 2000

[54] ARTIFICIAL INSEMINATION DEVICE FOR PRIVATE USE

[75] Inventors: Myeung-Sik Lee, Kyungki-Do; Soo-Bong Park, Suwon; Won-Kyong Chang, Suwon; Jin-Ki Park, Suwon; Yong-Yun Park, Suwon, all of Rep. of Korea

[73] Assignee: Rural Development Administration, Suwon, Rep. of Korea

[21] Appl. No.: 09/208,504

[22] Filed: Dec. 9, 1998

[30] Foreign Application Priority Data

Dec. 9, 1997 [KR] Rep. of Korea ...................... 97-66831

[51] Int. Cl.[7] ..................................................... A61B 17/43

[52] U.S. Cl. ................................................................ 600/35

[58] Field of Search ......................... 600/33–35; 119/174

[56] References Cited

U.S. PATENT DOCUMENTS 5,899,848 5/1999 Haubrich .................................. 600/35

*Primary Examiner*—John P. Lacyk

*Attorney, Agent, or Firm*—Nawrocki, Rooney & Sivertson, P.A.

[57] ABSTRACT

An artificial insemination device for private use which is capable of allowing unskilled persons to achieve an artificial insemination of livestock such as cattle, horses, and deer, etc. in a simple and easy manner using frozen semen of those livestock. The device includes an in-vagina insert unit inserted into the vagina of a female to be inseminated upon injecting semen into the female, and a semen injection unit inserted into the womb canal of the female through the in-vagina insert unit upon injecting semen into the female. The in-vagina insert unit includes a hollow insert body, and an insert tube slidably fitted at its rear end in a front end of the insert body in such a manner that its length protruded from the insert body is adjustable in accordance with the depth of the vagina of the female. The semen injection unit includes an elongated semen injection tube connected at a rear end thereof to an injector, and a guide/nozzle member separably coupled to a front end of the semen injection tube. The guide/nozzle member guides an insertion of the semen injection tube into the womb canal of the female.

9 Claims, 7 Drawing Sheets

ARTIFICIAL INSEMINATION DEVICE FOR PRIVATE USE

BACKGROUND OF THE INVENTION

1. Field of the Invention

The present invention relates to an artificial insemination device for private use which is capable of allowing unskilled persons to achieve an artificial insemination of livestock such as cattle, horses, and deer, etc. in a simple and easy manner using frozen semen of those livestock.

2. Description of the Prior Art

Generally, the term "artificial insemination of livestock" means a method for inseminating a female by injecting semen mechanically collected from a male into the genital of the female (womb canal) using an injector, in place of a direct copulation of the female with the male. The collected semen is preserved in a frozen state, and thawed upon using it.

Such an artificial insemination of livestock is generally performed on farms. For such an artificial insemination of livestock, frozen semen of a superior domestic animal is supplied to livestock breeders. Since this artificial insemination enables an improvement in the quality of livestock as well as a reliable pregnancy, it is encouraged for an increase in income and an increase in competitiveness.

Conventional artificial insemination methods using frozen semen include a recto-vaginal injection method, an injection method using a colposcope, and an injection method using pincers.

The colposcope-using injection method uses a vagina dilator adapted to dilate the vagina of a female. In accordance with this injection method, a semen injector is inserted into the dilated vagina while flashing a lamp or a colposcope lamp in the interior of the vagina, thereby observing the inlet of the womb canal disposed at a deep portion of the vagina. In such a manner, semen is injected into the womb through the inlet of the womb canal. In this method, however, the semen injection is troublesome and hazardous because the user carries out the semen injection while observing the inlet of the womb canal at a position close to the animal. Due to such a troublesome and hazardous semen injection, it is difficult to achieve an easy insemination.

The pincers-using injection method achieves a semen injection by drawing the upper portion of the womb canal inlet of an animal up to the vulva, using pincers, under the condition in which the vagina is dilated, and then inserting a semen injector into the drawn womb canal inlet. For this reason, the animal suffers severe pain. In severe cases, the animal may be injured, thereby resulting in bleeding or suppuration thereof.

Due to the above mentioned problems involved in the colposcope and pincers-using injection methods, the recto-vaginal injection method have been most commonly used. In accordance with the recto-vaginal injection method, it is required to remove dung from the rectum of an animal upon an artificial insemination. After removing dung from the rectum, the user finds the womb canal while inserting one hand into the rectum, so that he grasps the womb canal. Under this condition, the user inserts a semen injector into the vagina, using the other hand, and then injects semen into the womb canal. Thus, the user carries out the semen injection only by his experience in accordance with this recto-vaginal injection method.

In this recto-vaginal injection method, the success of an artificial insemination depends on whether or not semen is well injected into the womb canal.

However, this method is troublesome in that it is required to remove dung from the rectum. Furthermore, this method requires much experience and expert skill for the insertion of the semen injector, which has a simple cylindrical tube structure, into the womb canal disposed at a deep portion of the vagina. For this reason, it is difficult to use this method for an artificial insemination of livestock on general farms.

Due to such a difficulty in the artificial insemination, this method can be effectively achieved only by skilled persons. For this reason, an increase in the costs occurs. Moreover, it is difficult to carry out a desired artificial insemination at a proper time.

SUMMARY OF THE INVENTION

The present invention has been made in view of the problems involved in the above mentioned conventional methods, and, therefore, an object of the invention is to provide an artificial insemination device for private use which is capable of allowing unskilled persons to achieve an artificial insemination of livestock such as cattle, horses, and deer, etc. in a simple, easy, and reliable manner using frozen semen of those livestock.

Another object of the invention is to provide an artificial insemination device for private use which is capable of adjusting its length inserted into the vagina of an animal to be inseminated, in accordance with the size (depth) of the vagina determined by the kind of the animal.

In accordance with the present invention, these objects are accomplished by providing an artificial insemination device for private use adapted to achieve an artificial insemination of livestock, such as cattle, horses, and deer, etc., by injecting semen of a male into the womb canal of a female using an injector in which the semen is contained after being thawed from a frozen state, comprising: an in-vagina insert unit inserted into the vagina of the female to be inseminated upon injecting semen into the female, the in-vagina insert unit comprising a longitudinally extending hollow insert body being open at front and rear ends thereof, an insert tube being open at front and rear ends thereof and slidably fitted at the rear end thereof in the front end of the insert body in such a manner that its length protruded from the insert body is adjustable in accordance with the depth of the vagina of the female, and a guide passage defined in the insert body and the insert tube; and a semen injection unit inserted into the womb canal of the female through the rear end of the insert body and the guide passage of the in-vagina insert unit upon injecting semen into the female, the semen injection unit comprising an elongated semen injection tube connected at a rear end thereof to the injector, and a guide/nozzle member separably coupled to a front end of the semen injection tube and adapted to guide an insertion of the semen injection tube into the womb canal of the female and to inject the semen fed thereto from the semen injection tube into the womb canal of the female.

BRIEF DESCRIPTION OF THE DRAWINGS

Other objects and aspects of the invention will become apparent from the following description of embodiments with reference to the accompanying drawings in which.

DESCRIPTION OF THE PREFERRED EMBODIMENTS

Figure 1:
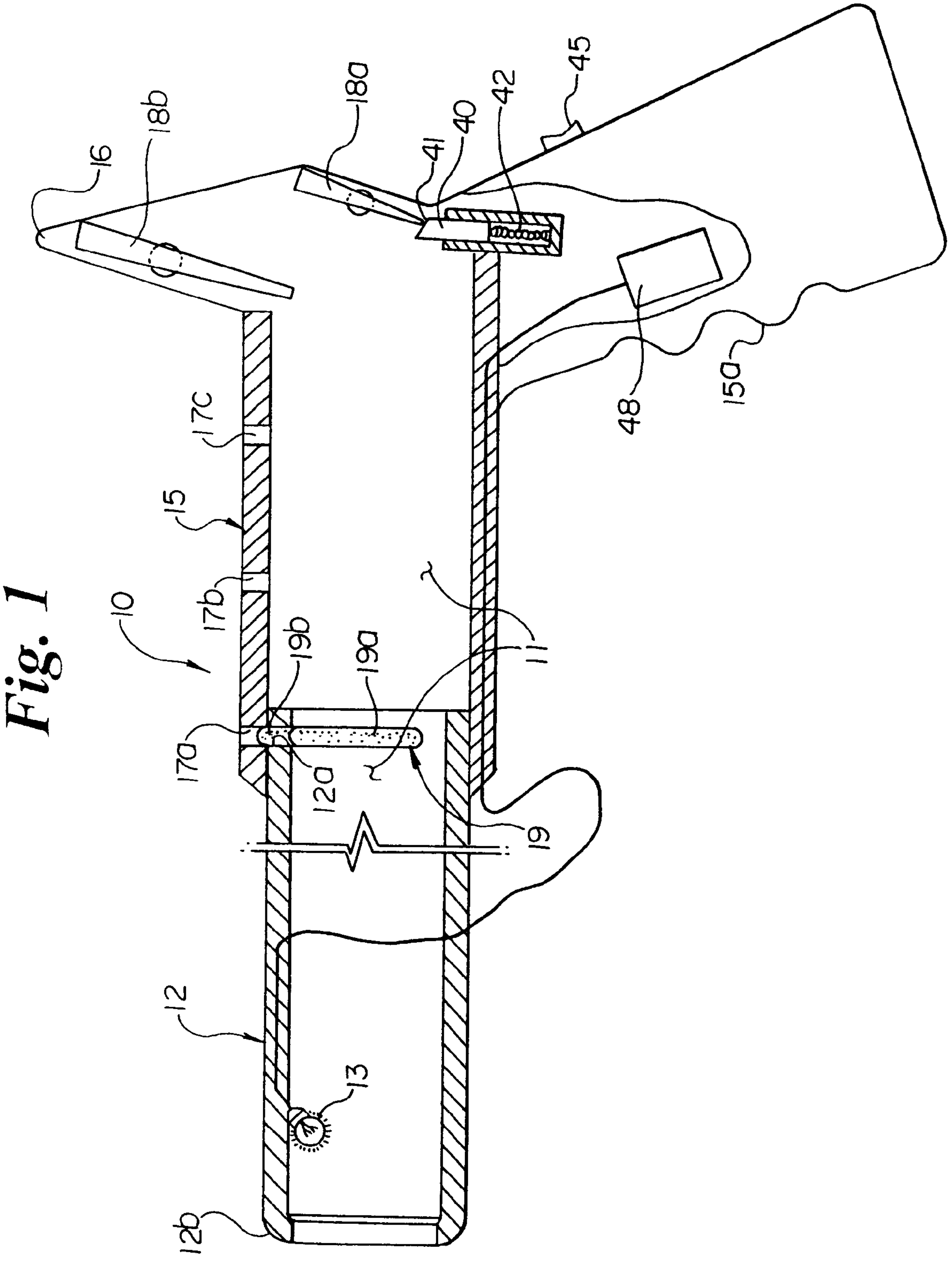
FIG. 1 is a sectional view illustrating an in-vagina insert unit included in an artificial insemination device according to the present invention.
Figure 2:
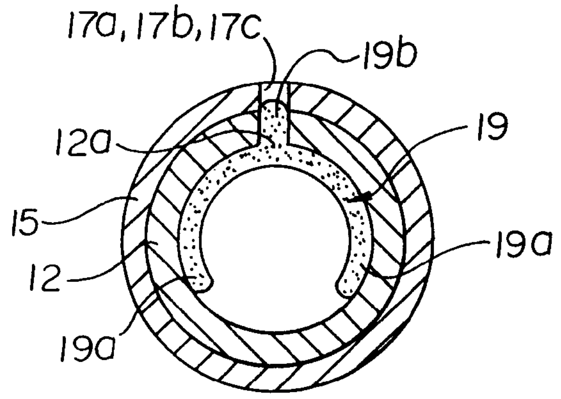
FIG. 2 is a cross-sectional view taken along the line A—A of FIG. 1.
Figure 3:
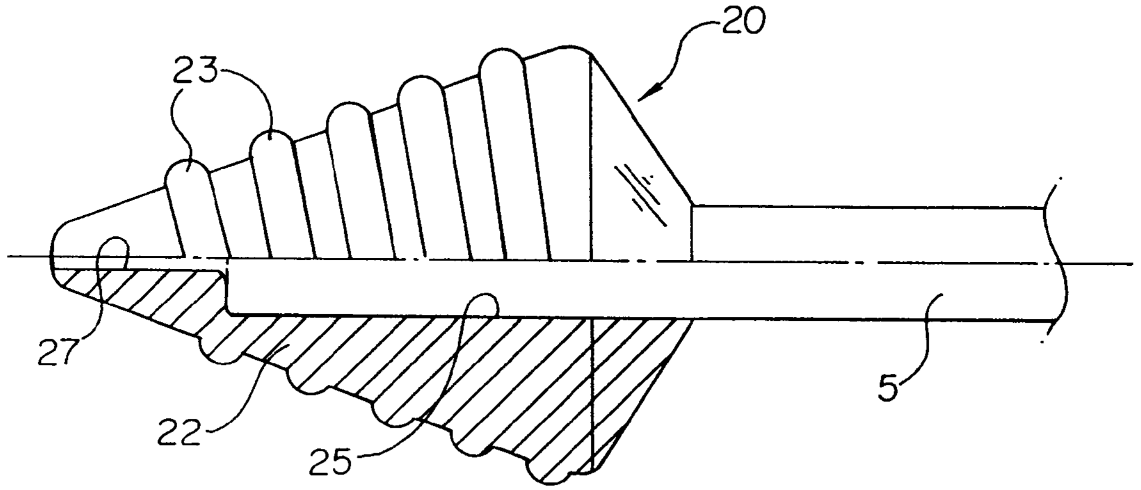
FIG. 3 is a sectional view illustrating a semen injection unit included in the artificial insemination device of FIG. 1.

Referring to FIGS. 1 to 3, an artificial insemination device for private use according to an embodiment of the present invention is illustrated, respectively. The artificial insemination device is adapted to achieve an artificial insemination of livestock, such as cattle, horses, and deer, etc., by injecting semen of a male into the womb canal of a female using an injector in which the semen is contained after being thawed from a frozen state.

In accordance with the illustrated embodiment of the present invention, the artificial insemination device includes an in-vagina insert unit 10, and a semen injection unit 20 inserted into the in-vagina insert unit 10 upon injecting semen into a female to be inseminated.

The in-vagina insert unit 10 includes a hollow insert body 15 provided at a rear end thereof with a tube-shaped upward extension 16. The upward extension 16 extends upwardly while being rearwardly inclined in such a manner that it has a higher front wall portion and a lower rear wall portion. The front wall portion of the upward extension 16 serves as a stopper for limiting an insertion of the in-vagina insert unit 10 into the vagina of a female to be inseminated. The in-vagina insert unit 10 also includes an insert tube 12 slidably fitted at a rear end thereof in the front end of the insert body 15 in such a manner that its length protruded from the insert body 15 is adjustable in accordance with the depth of the vagina of the female. The insert body 15 and insert tube 12 define therein a guide passage 11 for guiding the semen injection unit 20 upon injecting semen into the female to be inseminated.

As shown in FIG. 3, the semen injection unit 20 includes an elongated semen injection tube 5 connected at the rear end thereof to an injector (not shown) having a conventional configuration, and a conical guide/nozzle member 22 coupled to the front end of the semen injection tube 5.

Referring to FIG. 1 again, the insert body 15 of the in-vagina insert unit 10 is provided at its front portion with a plurality of longitudinally spaced locking holes 17*a*, 17*b* and 17*c*. The insert tube 12 is provided at its rear end with an engagement hole 12*a*.

A locking member 19 is fitted in the insert tube 12 at the rear end of the insert tube 12. As best shown in FIG. 2, the locking member 19, which is made of an elastic material, has a pair of support portions 19*a* and 19*b* elastically fitted in the insert tube 12, and a protrusion 19*b* upwardly protruded from a junction between the support portions 19*a* and 19*b* and provided with a round tip. The protrusion 19*b* of the locking member 19 extends upwardly through the engagement hole 12*a* of the insert tube 12 in such a manner that its round tip extends upwardly beyond the engagement hole 12*a*. The round tip of the protrusion 19*b* is engaged with a selected one of the locking holes 17*a* to 17*c* of the insert body 15, so that the insert tube 12 is locked at a desired position with respect to the insert body 15.

At the front portion of the insert tube 12, a lamp 13, which is configured to turn on and off selectively, is mounted in the insert tube 12. At the rear end of the insert body 15 corresponding to the rear end of the guide passage 11, a first mirror 18*a* is mounted on the inner surface of the rear wall portion of the upward extension 16 in such a fashion that it is rearwardly inclined at a desired angle with respect to a vertical line. A second mirror 18*b* is mounted on the inner surface of the front wall portion of the extension 16 in such a fashion that it is aligned with the reflecting optical axis of the first mirror 18*a* while being rearwardly inclined at a desired angle with respect to a vertical line. The first and second mirrors 18*a* and 18*b* are configured to adjust their inclination angles, respectively.

An opening, which is not denoted by any reference numeral, is formed through a junction between the rear end of the insert body 15 and the rear wall portion of the upward extension 16. A stopper pin 40 is slidably mounted to the junction between the rear end of the insert body and the rear wall portion of the upward extension 16 near the opening in such a fashion that the stopper pin 40 extends upwardly across the opening. The stopper pin 40 is always upwardly urged across the opening by a compression coil spring 42. The stopper pin 40 is provided at its upper end with a downwardly and rearwardly inclined surface 41. This stopper pin 40 having such a configuration serves to allow the guide/nozzle member 22 to enter the in-vagina insert unit 10 while preventing it from being removed out of the in-vagina insert unit 10. This function of the stopper pin 40 is adapted to separate the guide/nozzle member 22 from the semen injection tube 5.

As shown in FIG. 3, the conical guide/nozzle member 22 has a coupling hole 25 longitudinally formed through the conical guide/nozzle member 22 and adapted to receive the front end of the semen injection tube 5, and a semen injection port 27 formed at the front end of the conical guide/nozzle member 22 while communicating with the coupling hole 25.

The conical guide/nozzle member 22 is divided into a front portion made of an opaque material and a rear portion made of a transparent material. The conical guide/nozzle member 22 is also provided at its outer surface with a spiral thread 23 having a round surface so that it serves as a guide when the front end of the semen injection tube 5 is inserted into the womb canal of a female to be inseminated. The conical guide/nozzle member 22 also serves to inject semen fed thereto from the semen injection tube 5 into the womb canal of the female.

Figure 4:
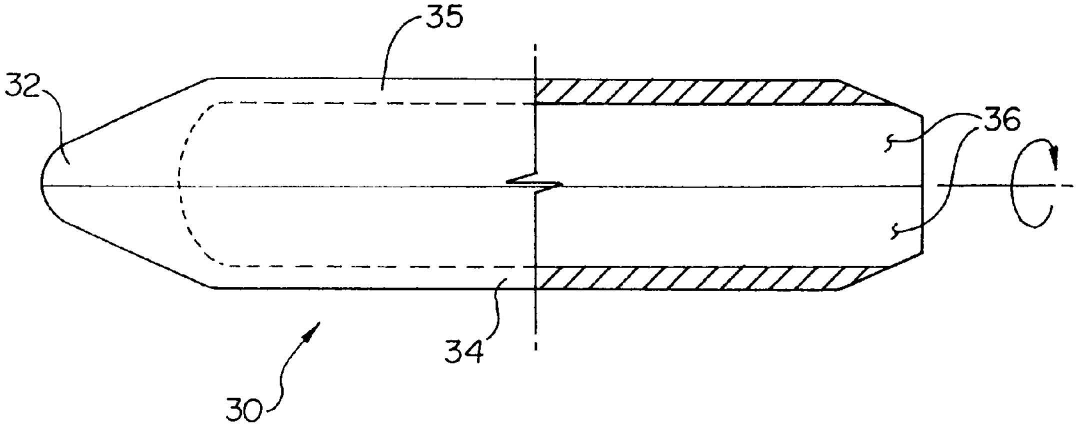
FIG. 4 is an insertion assistant member according to the present invention.

The artificial insemination device may also include an insertion assistant member 30 having a configuration as shown in FIG. 4. The insertion assistant member 30 is fitted around the insert tube 12 to facilitate an insertion of the in-vagina insert unit 10 into the vagina of a female to be inseminated. The insertion assistant member 30 consists of an upper cover 34 and a lower cover 35 hingably coupled to the upper cover 34. The insertion assistant member 30 has a front end 32 having a conical shape, and an open rear end. The insertion assistant member 30 defines therein a space for receiving the insert tube 12.

Figure 8:
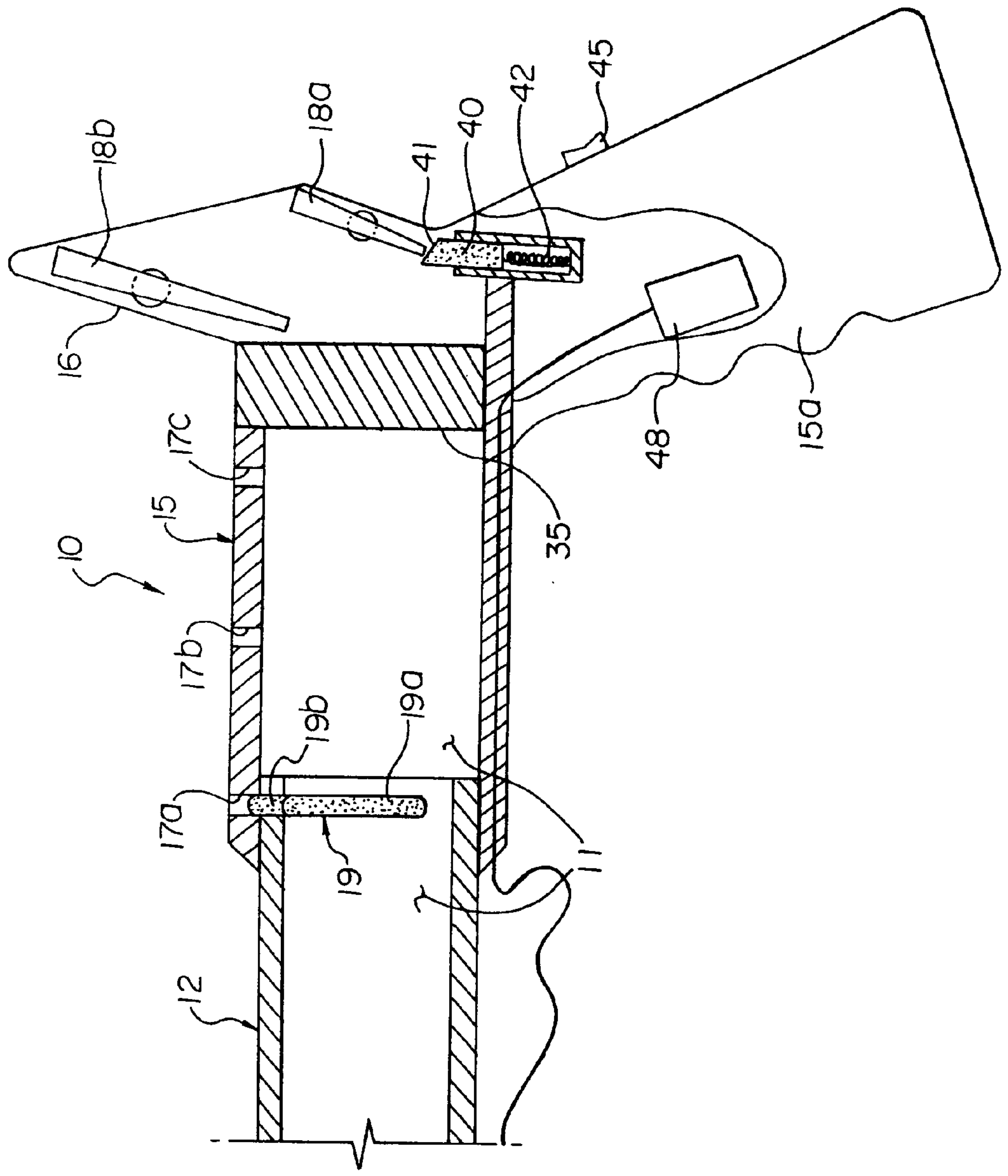
FIG. 8 is a sectional view illustrating another embodiment of the in-vagina insert unit according to the present invention.

Referring to FIG. 8, another embodiment of the insert body 15 of the in-vagina insert unit 10 is illustrated. In this case, a ventilation 35 is provided at a portion of the insert body 15 disposed near the first and second mirrors 18*a* and 18*b*. The ventilation 35 may consist of a net member having a cross-sectional shape substantially identical to that of the insert body 15. The ventilation 35 serves to allow warm air flowing rearwardly toward the first and second mirrors 18*a* and 18*b* to be outwardly vented before it reaches the first second mirrors 18*a* and 18*b*, thereby preventing the first and second mirrors 18*a* and 18*b* from being steamed up with the air.

Although not shown, heating plates are installed on respective back sides of the first and second mirrors 18*a* and 18*b* opposite to the reflecting surfaces of those mirrors, in order to heat the first and second mirrors 18*a* and 18*b*. By these heating plates, it is also possible to prevent the first and second mirrors 18*a* and 18*b* from being steamed up with air.

In the drawings, the reference numeral 12*b* denotes a round surface formed at the front end of the insert tube 12 and adapted to facilitate an insertion of the insert tube 12 into the vagina of a female to be inseminated. The reference numeral 15*a* denotes a grip formed at the rear end of the insert body 15 of the in-vagina insert unit 10. The reference numeral 45 denotes a switch 48 coupled between a power supply 48 and the lamp 13 disposed in the insert tube 15 in order to turn on and off the lamp 13.

Now, an operation of the artificial insemination device having the above mentioned configuration will be described.

Where it is desired to carry out an artificial insemination of a female which may be livestock such as cattle, horses, and deer, etc., the total length of the in-vagina insert unit 10 is first adjusted in accordance with the depth of the vagina of the female to be inseminated. This can be achieved by adjusting the length of the insert tube 12 forwardly protruded from the insert body 15. This will be described in more detail.

The protrusion 19*b* of the locking member 19 elastically fitted in the insert tube 12 is depressed so that it is separated from the locking hole 17*a*, 17*b* or 17*c* of the insert body 15 in which it is received, thereby causing the insert tube 12 from being released from the insert body 15. At this time, the locking member 19 is positioned in such a manner that its support portions 19*a* are elastically maintained at a lowered position in the insert tube 12 while its protrusion 19*b* is still engaged with the engagement hole 12*a* of the insert tube 12.

In this state, the insert tube 12 can slide along the insert body 15. When the insert tube 12 slides along the insert body 15 in such a fashion that its engagement hole 12*a* is aligned with a desired one of the locking holes 17*a* to 17*c* of the insert body 15 corresponding to a desired total length of the in-vagina insert unit 10, the protrusion 19*b* of the locking member 19 moves upwardly through the selected locking hole of the insert body 15 by virtue of the elasticity of the locking member 19. Accordingly, the protrusion 19*b* of the locking member 19 engages with the selected locking hole of the insert body 15, thereby causing the insert tube 12 to be locked to the insert body 15. Thus, the total length of the in-vagina insert unit 10 is adjusted.

Figure 5:
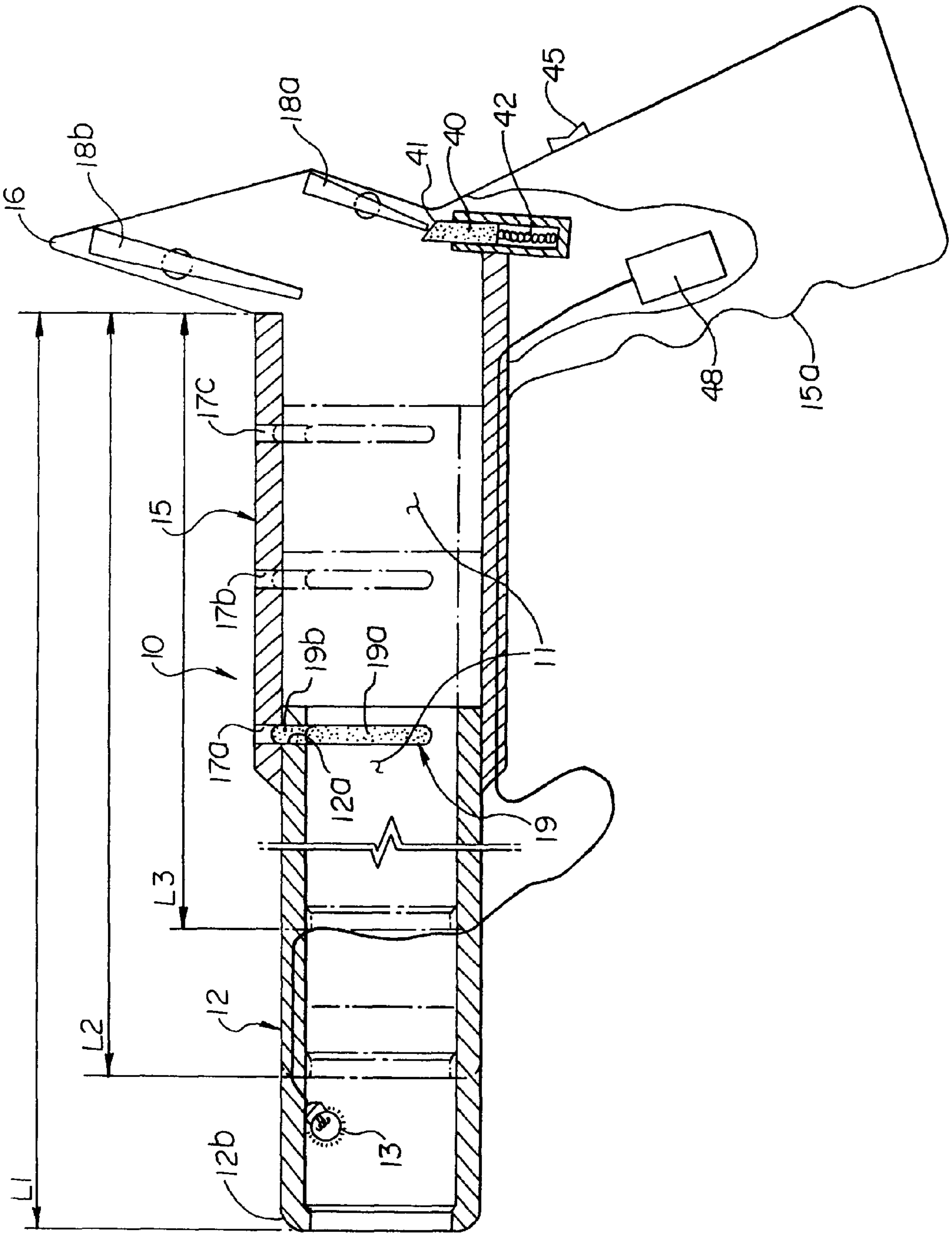
FIG. 5 is a sectional view illustrating a length adjustment of the in-vagina insert unit in accordance with the present invention.

The total length of the in-vagina insert unit 10 is gradually reduced from "L1" to "L3" in the order of the first locking hole 17*a*, the second locking hole 17*b*, and the third locking hole 17*c*, at which the insert tube 12 is locked, as shown in FIG. 5. Here, "L1" corresponds to a total length of the in-vagina insert unit 10 when the insert tube 12 is locked at the first locking hole 17*a* whereas "L3" corresponds to a total length of the in-vagina insert unit 10 when the insert tube 12 is locked at the third locking hole 17*c*. In FIG. 5, "L2" corresponds to a total length of the in-vagina insert unit 10 when the insert tube 12 is locked at the second locking hole 17*b*.

The number and space of such locking holes may be optionally determined.

After adjusting the length of the in-vagina insert unit 10 in accordance with the depth of the vagina of the female to be inseminated, the insertion assistant member 30 is fitted around the in-vagina insert unit 10 in such a fashion that the insert tube 12 is received in the space 36.

Figure 6:
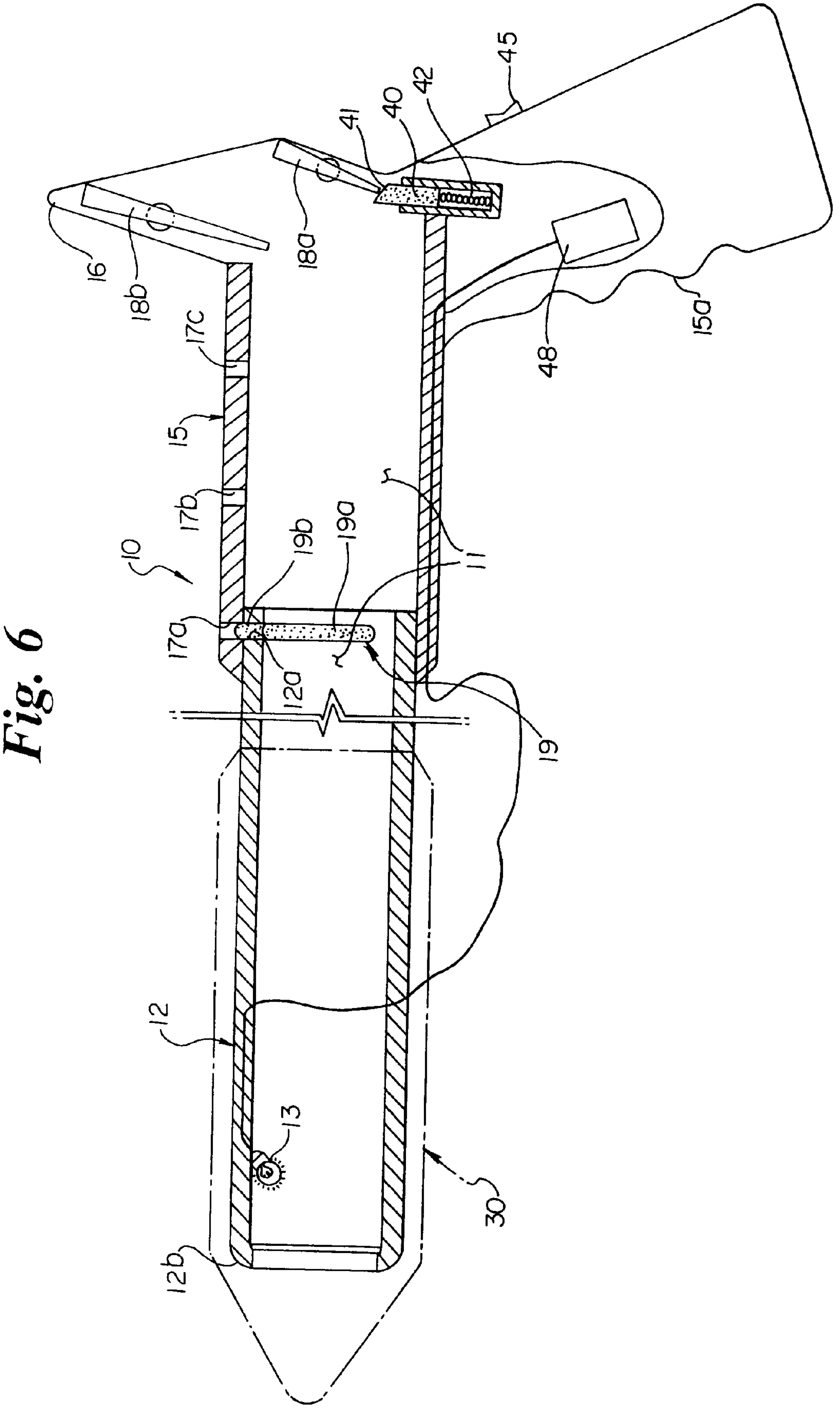
FIG. 6 is a sectional view illustrating a condition in which the insertion assistant member of FIG. 4 is fitted around the in-vagina insert unit in accordance with the present invention.

Thereafter, the insertion assistant member 30 is inserted into the vagina of the female. This insertion is conveniently carried out under the condition in which the user grasps the grip 15*a* of the in-vagina insert unit 10 by hand. The insertion of the insertion assistant member 30 can also be easily carried out by virtue of the conical shape of the front end 32 of the insertion assistant member 30 (FIG. 6).

After completing the insertion of the insertion assistant member 30, the user opens the upper and lower covers 34 and 35 of the insertion assistant member 30 by hingably moving them with respect to each other. In this state, the insertion assistant member 30 can be separated from the vagina of the female while leaving the insert tube 12 of the in-vagina insert unit 10 in the vagina.

Although the insertion assistant member 30 is used to facilitate the insertion of the in-vagina insert unit 10 in the above case, it may also be possible to directly insert the in-vagina insert unit 10 into the vagina of the female without using the insertion assistant member 30.

Once the in-vagina insert unit 10 is partially inserted into the vagina in the above mentioned manner, it is further inserted into the vagina until the genital of the female comes into contact with the front wall portion of the upward extension 16. In this state, the front end of the insert tube 12 is positioned at the inlet of the womb canal. This can be possible by virtue of the fact that the total length of the in-vagina insert unit 10 is adjusted in accordance with the depth of the vagina.

Thereafter, the semen injection tube 5, to which the conical guide/nozzle member 22 is coupled, is inserted into the guide passage 11 defined in the in-vagina insert unit 10 through the opening formed at the rear end of the in-vagina insert unit 10. As mentioned above, the semen injection tube 5 is connected at its rear end to an injector (not shown) in which the semen of a superior male is contained after being thawed from a frozen state.

Although the stopper pin 40 of the clamp extends across the opening formed at the rear end of the in-vagina insert unit 10, the guide/nozzle member 22 can easily enter the guide passage 11 of the in-vagina insert unit 10 through the opening because its front end (namely, leading end) has a conical shape capable of coming into contact with the inclined surface of the stopper pin 40, thereby urging the stopper pin 40 to be retracted against the resilience of the compression coil spring 42.

Figure 7:
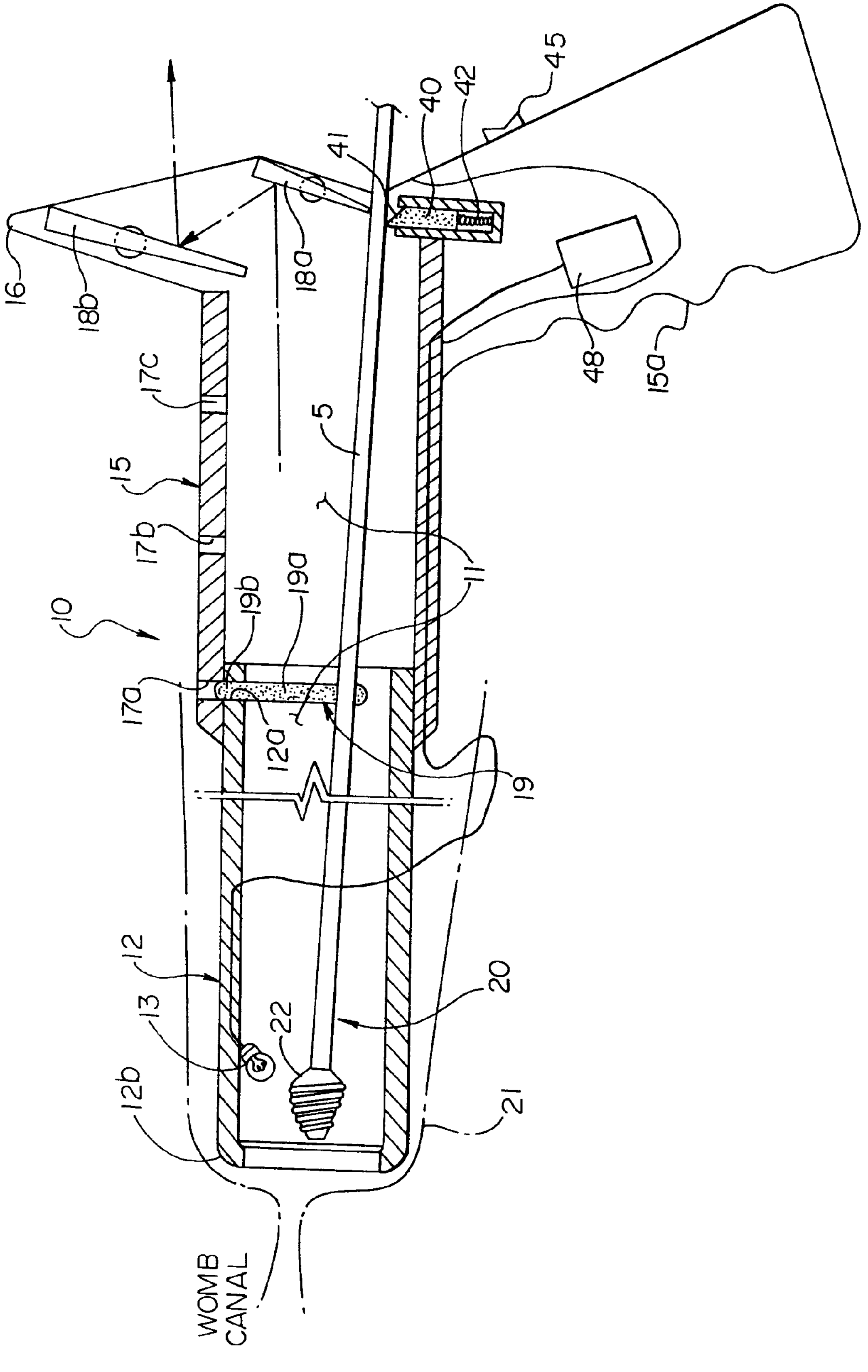
FIG. 7 is a sectional view illustrating an insertion of the semen injection unit into the in-vagina insert unit according to the present invention.

The insertion of the semen injection tube 5 is continued until the guide/nozzle member 22 reaches the inlet of the womb canal. Since the lamp 13 disposed at the front portion of the insert tube 12 is in its ON state during the insertion of the semen injection tube 5, the situation at the front portion of the insert tube 12 can be observed by the user via the first and second mirrors 18*a* and 18*b* (FIG. 7). Accordingly, it is possible to more easily carry out the insertion of the semen injection tube 5.

After the guide/nozzle member 22 reaches the inlet of the womb canal, a further insertion thereof is made so that it is inserted into the womb canal.

In this case, an easy insertion of the guide/nozzle member 22 into the womb canal is made even by an unskilled person without any pain suffered by the animal because the guide/nozzle member 22 has a conical shape. In particular, the user can surely observe the insertion of the guide/nozzle member 22 because the rear portion of the guide/nozzle member 22 is made of a transparent material. Thus, the insertion of the semen injection unit 20 can be more easily carried out.

Even in the case wherein the womb canal of the female to be inseminated is non-uniform, for example, inclined or bent, the semen injection tube 5 of the semen injection unit 20 can be easily inserted into the womb canal by virtue of the function of the guide/nozzle member 22. Furthermore, since the guide/nozzle member 22 is inserted into the womb canal while rotating by virtue of the spiral thread 23 formed thereon, it is also possible to prevent the guide/nozzle member 22 from being separated from the womb canal.

After the insertion of the guide/nozzle member 22 into the womb canal is completed as mentioned above, semen is injected from the semen injection unit 20 into the womb canal through the semen injection port 27. At this time, the injection of semen into the womb canal is surely carried out because the guide/nozzle member 22 is accurately inserted in the womb canal.

After the completion of the injection of semen into the womb canal, the guide/nozzle member 22 is removed from the womb canal. This removal of the guide/nozzle member 22 can be achieved by rearwardly drawing the semen injection tube 5 along the guide passage 11 of the in-vagina insert unit 10. When the semen injection tube 5 is further drawn in a state in which the guide/nozzle member 22 reaches the stopper pin 40 disposed at the rear end of the guide passage 11, the guide/nozzle member 22 is separated from the semen injection tube 5 because it is drawn, no longer, due to the stopper pin 40. Accordingly, only the semen injection tube 5 is removed from the in-vagina insert unit 10. The guide/nozzle member 22 is separately removed from the in-vagina insert unit 10 after removing the in-vagina insert unit 10 from the vagina.

After the removal of the semen injection tube 5, the in-vagina insert unit 10 is removed from the vagina. Thus, the artificial insemination is completed.

As apparent from the above description, the present invention provides an artificial insemination device for private use which is capable of allowing unskilled persons to achieve an artificial insemination of livestock such as cattle, horses, and deer, etc. in a simple and easy manner, without any pain suffered by the livestock, using frozen semen of those livestock. Accordingly, the present invention achieves an improvement in the quality of livestock as well as a reliable pregnancy.

Although the preferred embodiments of the invention have been disclosed for illustrative purposes, those skilled in the art will appreciate that various modifications, additions and substitutions are possible, without departing from the scope and spirit of the invention as disclosed in the accompanying claims.

What is claimed is:

1. An artificial insemination device for private use adapted to achieve an artificial insemination of livestock, such as cattle, horses, and deer, etc., by injecting semen of a male into the womb canal of a female using an injector in which the semen is contained after being thawed from a frozen state, comprising:

an in-vagina insert unit inserted into the vagina of the female to be inseminated upon injecting semen into the female, the in-vagina insert unit comprising a longitudinally extending hollow insert body being open at front and rear ends thereof, an insert tube being open at front and rear ends thereof and slidably fitted at a rear end thereof in the front end of the insert body in such a manner that its length protruded from the insert body is adjustable in accordance with the depth of the vagina of the female, and a guide passage defined in the insert body and the insert tube; and a semen injection unit inserted into the womb canal of the female through the rear end of the insert body and the guide passage of the in-vagina insert unit upon injecting semen into the female, the semen injection unit comprising an elongated semen injection tube connected at a rear end thereof to the injector, and a guide/nozzle member separably coupled to a front end of the semen injection tube and adapted to guide an insertion of the semen injection tube into the womb canal of the female and to inject the semen fed thereto from the semen injection tube into the womb canal of the female.

2. The artificial insemination device according to claim 1, wherein the in-vagina insert unit further comprises:

a lamp configured to turn on and off selectively and mounted in the insert tube at a front portion of the insert tube.

3. The artificial insemination device according to claim 1, wherein the in-vagina insert unit further comprises:

a plurality of longitudinally spaced locking holes provided at a front portion of the insert body;

an engagement hole provided at the rear end of the insert tube; and a locking member fitted in the insert tube at the rear end of the insert tube and engaged with a selected one of the locking holes aligned with the engagement hole, thereby causing the insert tube to be locked with respect to the insert body while being adjusted in a length thereof protruded from the insert body.

4. The artificial insemination device according to claim 3, wherein the locking member has a pair of support portions elastically fitted in the insert tube, and a protrusion upwardly protruded from a junction between the support portions, the protrusion extending upwardly through the engagement hole and having a round tip extending upwardly beyond the engagement hole to engage with a selected one of the locking holes.

5. The artificial insemination device according to claim 1, wherein the in-vagina insert unit further comprises:

means for separating the guide/nozzle member from the semen injection tube, the means comprising a stopper pin slidably mounted to the rear end of the insert body in such a manner that it extends upwardly across an opening defined by the rear end of the insert body, the stopper pin having at an upper end thereof with a downwardly and rearwardly inclined surface, and resilience means for always urging the stopper pin to extend upwardly across the opening.

6. The artificial insemination device according to claim 1, wherein the in-vagina insert unit further comprises:

a tube-shaped upward extension extending upwardly from the rear end of the insert body of the in-vagina insert unit while being rearwardly inclined in such a manner that it has a higher front wall portion and a lower rear wall portion, the upward extension being also provided with an opening formed at a junction between the rear end of the insert body and the rear wall portion of the upward extension, the opening being adapted to allow the semen injection unit to be inserted into the guide passage of the in-vagina insert unit;

a first mirror mounted on an inner surface of the rear wall portion of the upward extension in such a fashion that it is rearwardly inclined at a desired angle with respect to a vertical line;

a second mirror mounted on an inner surface of the front wall portion of the upward extension in such a fashion that it is aligned with a reflecting optical axis of the first mirror while being rearwardly inclined at a desired angle with respect to a vertical line; and means for adjusting respective inclination angles of the first and second mirrors.

7. The artificial insemination device according to claim 1, wherein the guide/nozzle member has a conical shape.

8. The artificial insemination device according to claim 1, wherein the guide/nozzle member is provided at an outer surface thereof with a spiral thread having a round surface.

9. The artificial insemination device according to claim 1, further comprising:

an insertion assistant member fitted around the insert tube upon an insertion of the in-vagina insert unit into the vagina of the female, the insertion assistant member consisting of an upper cover and a lower cover hingably coupled to the upper cover, the insertion assistant member also having a front end having a conical shape, and an open rear end, and the insertion assistant member defining therein a space for receiving the insert tube.

* * * * *